United States Patent
Maikap et al.

(10) Patent No.: US 9,595,565 B1
(45) Date of Patent: Mar. 14, 2017

(54) MEMORY STRUCTURE

(71) Applicant: CHANG GUNG UNIVERSITY, Taoyuan (TW)

(72) Inventors: Siddheswar Maikap, Taoyuan (TW); Subhranu Samanta, Taoyuan (TW)

(73) Assignee: Chang Gung University, Taoyuan (TW)

( * ) Notice: Subject to any disclaimer, the term of this patent is extended or adjusted under 35 U.S.C. 154(b) by 0 days.

(21) Appl. No.: 15/131,262

(22) Filed: Apr. 18, 2016

(51) Int. Cl.
   *H01L 27/24* (2006.01)
   *H01L 23/528* (2006.01)
   *H01L 45/00* (2006.01)
   *H01L 23/532* (2006.01)

(52) U.S. Cl.
   CPC ........ *H01L 27/2463* (2013.01); *H01L 23/528* (2013.01); *H01L 23/53257* (2013.01); *H01L 45/1233* (2013.01); *H01L 45/1253* (2013.01); *H01L 45/146* (2013.01)

(58) Field of Classification Search
   CPC ............................ H01L 27/2463; H01L 27/24
   See application file for complete search history.

(56) References Cited

U.S. PATENT DOCUMENTS

| | | | | | |
|---|---|---|---|---|---|
| 5,463,235 | A | * | 10/1995 | Ishii ...................... | H01L 27/115 257/300 |
| 5,739,566 | A | * | 4/1998 | Ota .................... | H01L 29/42324 257/298 |
| 5,838,611 | A | * | 11/1998 | Kanamori .......... | G11C 16/0491 257/E21.682 |
| 2001/0042882 | A1 | * | 11/2001 | Chang ............... | H01L 21/28273 257/315 |
| 2002/0022357 | A1 | * | 2/2002 | Iijima ............... | H01L 27/10855 438/622 |
| 2003/0161192 | A1 | * | 8/2003 | Kobayashi ......... | G11C 16/0475 365/200 |
| 2005/0219920 | A1 | * | 10/2005 | Sugawara ................ | G11C 7/14 365/200 |
| 2008/0200016 | A1 | * | 8/2008 | Arai ...................... | H01L 27/115 438/527 |
| 2009/0116273 | A1 | * | 5/2009 | Shiratake ................ | G11C 11/22 365/72 |
| 2010/0001371 | A1 | * | 1/2010 | Suzuki .................... | H01L 28/55 257/532 |

(Continued)

OTHER PUBLICATIONS

Maikap et al., "Cross-point Resistive Switching Memory Devices for Bio-Medical Applications", 18th International Workshop on Physics of Semiconductor Devices (IWPSD-2015), Dec. 7-10, 2015, J N Tata Auditorium, Indian Institute of Science (IISc), Bangalore, India.

(Continued)

*Primary Examiner* — Calvin Choi
*Assistant Examiner* — S. M. S Imtiaz
(74) *Attorney, Agent, or Firm* — Rosenberg, Klein & Lee (57) ABSTRACT

The present invention relates to a memory structure, which is a kind of resistive memory. A middle layer formed by a first dielectric film and a second dielectric film is included between the top and bottom electrodes. The material of the top electrode is iridium oxide. Thereby, preferred oxygen vacancy filament paths can be provided and thus exhibiting complementary resistive switching of memory arrays. Furthermore, the memory structure can be applied to biological tests.

9 Claims, 8 Drawing Sheets

(56) References Cited

U.S. PATENT DOCUMENTS

| | | | |
|---|---|---|---|
| 2014/0084948 A1* | 3/2014 | Tendulkar | H01L 22/34 |
| | | | 324/691 |
| 2016/0093707 A1* | 3/2016 | Ryu | H01L 21/28273 |
| | | | 257/316 |
| 2016/0225986 A1* | 8/2016 | Hsu | H01L 45/1253 |

OTHER PUBLICATIONS

Jana et al., "Evolution of complementary resistive switching characteristics using IrOx/GdOx/Al2O3/TiN structure", Applied Physics Letters, vol. 108, 011605 (Jan. 7, 2016).

* cited by examiner

MEMORY STRUCTURE

FIELD OF THE INVENTION

The present invention relates generally to a memory structure, and particularly to a memory structure adopting iridium oxide as the top electrode and having cross points for biological tests.

BACKGROUND OF THE INVENTION

In general, memories can be divided into two major types. One is the volatile memory; the other is the nonvolatile memory. The difference between the two is that when the power is broken, the data stored in a volatile memory will disappear, whereas that in a nonvolatile memory won't. Once the power is recovered, the data stored in a nonvolatile memory can be accessed.

Volatile memories include dynamic random access memories (DRAM) and static random access memories (SRAM). Their advantages include fast access and low price. On the other hand, nonvolatile memories according to the prior art include read only memories (ROM) and flash memories. The USB disks normally seen adopt flash memories. The main technology is the NAND technology, which uses floating-gate transistors to store data. According to the quantity of electrons stored in the semiconductor oxide layer or metal layer, the signals of 0 and 1 can be discriminated. The drawbacks of the technology include high operating voltages, low speed, and degraded data retention due to thinning of the tunneling oxide in the process of device miniaturization.

Accordingly, in order to maintain the advantages of current memories and improve the problems of flash memories, scientists are devoted in developing novel nonvolatile memories. Presently, novel nonvolatile memories can be classified into four types: ferroelectric RAM (FERAM), magnetoresistive RAM (MRAM), phase-change RAM (PCRAM), and resistive RAM (RRAM).

Among the memories, RRAM is the simplest in terms of structure. It usually adopts low-activity hard-to-oxidize metals, such as Pt and TiN, as the top and bottom electrodes; metal oxides, such as NiO, $TiO_2$, $HfO_2$, $Ta_2O_5$, $ZrO_2$, $Al_2O_3$ are mostly adopted as the middle oxide layer. The resistance transformation mechanism of an RRAM depends on the movement of oxygen ions in the middle oxide layer. By applying a bias on the top electrode, the oxygen ions will move under the action of the electric field. After they move away, the original sites will form oxygen vacancies, which can be used as the path for electron movement. Alternatively, a highly conductive anaerobic phase can be formed in the electrolyte. The oxygen vacancies continue to accumulate, leading to the formation of conductive channels. The device transforms from the high-resistive state to the low-resistive state. Then a reverse bias is applied, which changes the moving direction of the oxygen ions and enables the oxygen ions to recover the oxygen vacancies. Consequently, the conductive channels are broken, and the device transforms from the low-resistive state to the high-resistive state. RRAM owns the property of bipolar transformation. The concentration of oxygen vacancies determines the electrical characteristics of such devices. If the concentration is too low, devices will become unstable, and the endurance will degrade as well.

SUMMARY

An objective of the present invention is to provide a memory structure, which include an interface between iridium and a specific dielectric material. Thereby, preferred oxygen vacancy filament paths at the dielectric/metal interfaces can be provided and thus exhibiting complementary resistive switching of memory.

Another objective of the present invention is to provide a memory structure. The memory structure is tested for over 1000 cycles using pulses having 1-microsecond period, and hence having substantial reliability.

A further objective of the present invention is to provide a memory structure, which includes a plurality of cross points. The plurality of cross points can be used as a portion of a biochip. A sample can be placed on the bit line, which is used as the top electrode. The iridium oxide in the material of the bit line will be involved in oxidation and reduction reactions and producing detectable current or voltage changes. As a result, the concentration of the test target, for example, pH change in analyte, the enzyme LOXL2, sarcosine or other cancer, in the sample can be given and used for evaluating the possibility of suffering from breast, prostate or other cancers.

Accordingly, the present invention discloses a memory structure, which comprises a substrate, a plurality of word lines, a plurality of bit lines, and a plurality of middle layers. The plurality of word lines are disposed in parallel on the substrate. The plurality of bit lines are disposed in parallel on the substrate, and covering and perpendicular to the plurality of word lines at a plurality of cross points. The material of the plurality of bit lines is iridium oxide. Other materials instead of iridium oxide such as ruthenium oxide, platinum, palladium, cobalt, rhenium, rhodium, graphene, and so on can be chosen. The plurality of middle layers are disposed at the plurality of cross points and located between the plurality of word lines and the plurality of bit lines. From bottom to top, the plurality of middle layers include a first dielectric film and a second dielectric film. The material for the first dielectric film is aluminum oxide ($Al_2O_3$) or silicon dioxide ($SiO_2$) because large energy gap material with negligible defects is preferable. The material of the second dielectric film is selected from the group consisting of gadolinium oxide, hafnium oxide, tantalum oxide, nickel oxide, zirconium oxide, chromium oxide, titanium oxide, tungsten oxide, cerium oxide, germanium oxide, and so on. Basically, the characteristics of second dielectric film are lower energy gap and more defective or this layer will be used as a oxygen vacancy supplier.

In addition, when the present invention applied to a biochip, the structure comprises a substrate, a plurality of word lines, a plurality of bit lines, and a plurality of middle layers. The plurality of word lines are disposed in parallel on the substrate. The plurality of bit lines are disposed in parallel on the substrate, and covering and perpendicular to the plurality of word lines at a plurality of cross points. The material of the plurality of bit lines is iridium oxide. The plurality of middle layers are disposed at the plurality of cross points and located between the plurality of word lines and the plurality of bit lines. From bottom to top, the plurality of middle layers include a first dielectric film and a second dielectric film. The first dielectric film is the same as above. The material of the second dielectric film is the same of the memory structure above. A top surface of the plurality of bit lines is used for contacting a sample.

DETAILED DESCRIPTION

In order to make the structure and characteristics as well as the effectiveness of the present invention to be further understood and recognized, the detailed description of the present invention is provided as follows along with embodiments and accompanying figures.

Figure 1:
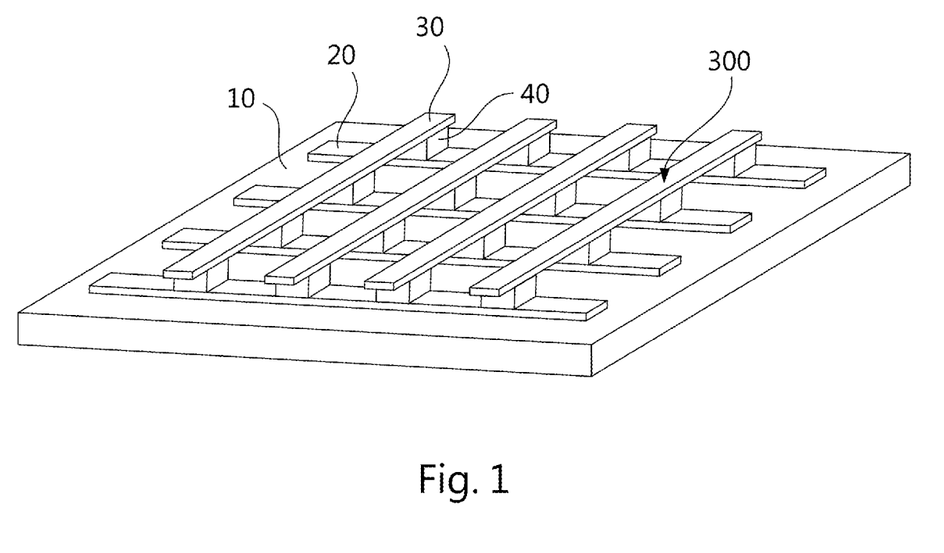
FIG. 1 shows a schematic diagram of a portion of the memory structure according to a preferred embodiment of the present invention.

First, please refer to FIG. 1. According to a preferred embodiment of the present invention, the disclosed memory structure comprises a substrate 10, a plurality of word lines 20, a plurality of bit lines 30, and a plurality of middle layers 40. The plurality of word lines 20 are disposed on the substrate 10. The plurality of bit lines 30 are disposed on the plurality of word lines 20. The plurality of middle layers 40 are disposed between the plurality of word lines 20 and the plurality of bit lines 30. Moreover, the plurality of word lines 20 and the plurality of bit lines 30 are disposed in parallel on the substrate 10, respectively. Nonetheless, their parallel directions are perpendicular to each other and hence producing cross points. Each cross point represents a storage location for memory. Please also refer to FIG. 2. The plurality of word lines 20 and the plurality of bit lines 30 are interlaced perpendicularly and producing a plurality of cross points 300 covering the plurality of word lines 20.

Figure 2:
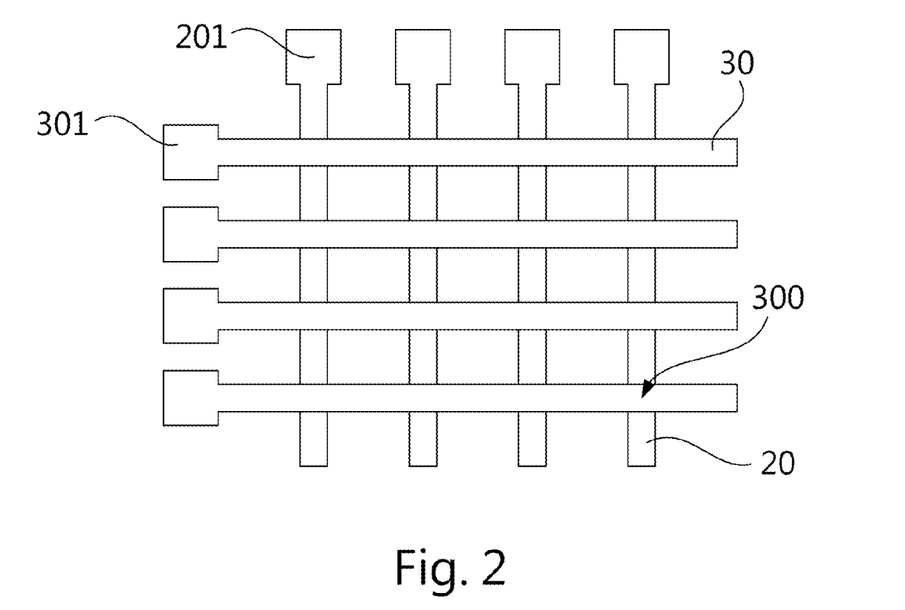
FIG. 2 shows a schematic diagram of a portion of the memory structure according to a preferred embodiment of the present invention, used for illustrating the electrodes located on the periphery.

As shown in FIG. 2, one or more end of the word line 20 includes a bottom electrode 201; one or more end of the bit line 30 includes a top electrode 301. They are used for connecting to external circuits, respectively.

Figure 3:
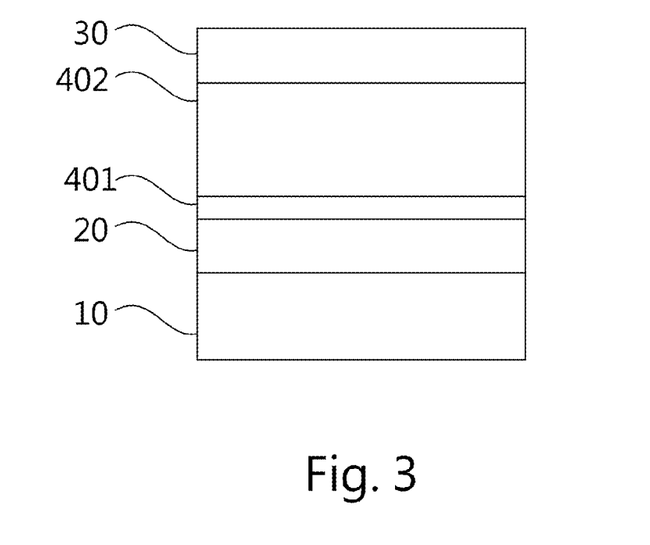
FIG. 3 shows a schematic diagram of the stack structure of the middle layer according to a preferred embodiment of the present invention.

Please refer to FIG. 3. In the stack structure of a single cross point, the substrate 10 at the bottom-most layer is used for carrying devices. The word line 20 on the substrate 10 is used as the bottom electrode of the memory. According to a preferred embodiment of the present invention, titanium nitride (TiN) or other inert electrodes is adopted as the material of the word line 20. The middle layer 40 on the word line 20 includes one or more first dielectric film 401 and a second dielectric film 402. The material of the first dielectric film 401 is aluminum oxide or silicon dioxide; the material of the second dielectric film 402 is gadolinium oxide, hafnium oxide, tantalum oxide, nickel oxide, zirconium oxide, chromium oxide, titanium oxide, tungsten oxide, cerium oxide, or germanium oxide. The bit line 30, which is used as the top electrode of the memory, is located on the second dielectric film 402. The material of the bit line 30 is iridium oxide. Another dielectric layer at the second dielectric/iridium oxide interface can generally be created which is also important for complementary resistive switching memory for cross-point arrays. In addition, for other bit line material 30 the first dielectric film 401 can be deposited further on the second dielectric 402.

The memory according to the present invention owns the feature of a complementary resistive switching (CRS) memory. A general CRS memory connects reversely two bipolar switching (BS) resistive memories in series to form a device, for example, the stack structure of top electrode/dielectric/metal/dielectric/bottom electrode. According to the present invention, no metal material is required inside the dielectrics. For example, the copper (or TaN) in the above example can be omitted. Once the specific materials are chosen, the stack structure of top electrode/dielectric/dielectric/bottom electrode or top electrode/dielectric/dielectric/dielectric/bottom electrode is formed at each cross point. Furthermore, the present invention can be regarded as an improvement for a BS memory. A normal BS memory owns a top electrode/dielectric/bottom electrode stack structure. According to the present invention, by using specific materials and the addition of a dielectric film, the stack structure of top electrode/dielectric/dielectric/dielectric/bottom electrode can achieve the feature of a CRS memory.

A CRS memory includes four states: ON, OFF, 0, and 1. The OFF state occurs only in a non-initialized CRS memory. After the initialization process, this state will not appear in the operations of a CRS memory. The states 0 and 1 represent normal logic storage signals. The ON state appears only while reading a CRS memory.

Figure 4:
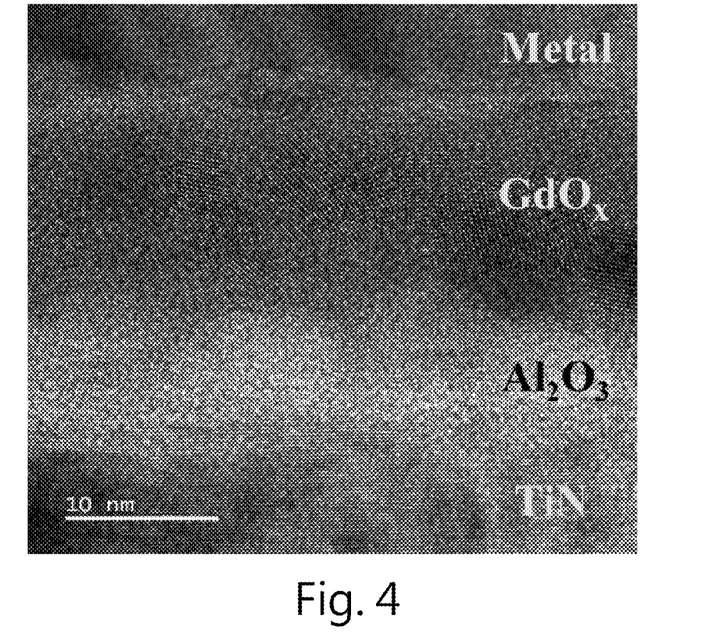
FIG. 4 shows a microscopic picture of a portion of the stack structure according to a preferred embodiment of the present invention.
Figure 5:
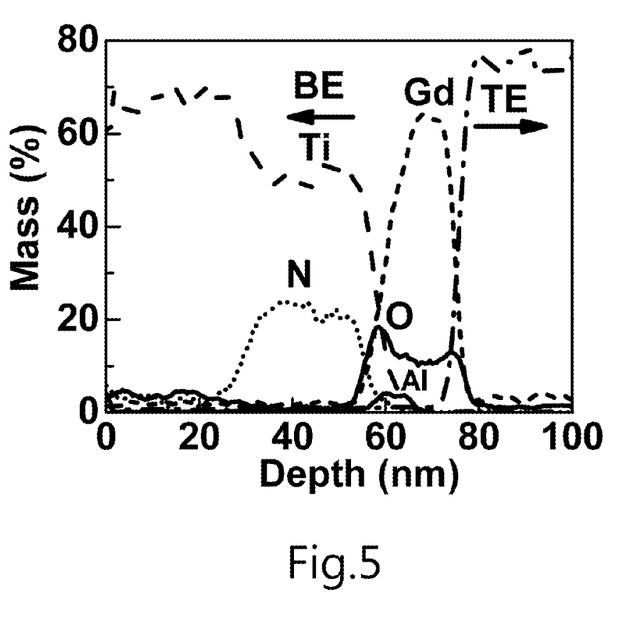
FIG. 5 shows an EDS depth profile from the bottom electrode to the top electrode according to a preferred embodiment of the present invention.

In an embodiment of preparing the memory according to the present invention, a silicon dioxide file with a thickness of approximately 200 nanometers is deposited on a silicon substrate in at an ambient temperature of 950° C. Then a titanium film of approximately 170 nanometers is deposited on the silicon dioxide/silicon substrate. Next, by using RF spray coating, an approximately 30-nanometer titanium nitride layer is deposited and used as the bottom electrode. Afterwards, an approximately 150-nanometer silicon dioxide film is deposited on the bottom electrode formed by titanium nitride, where the silicon dioxide film includes 8-micron-squared via holes. The pattern of the bottom electrode can be formed by etching after photolithography. Then, an approximately 2-nanometer aluminum oxide is deposited by RF spray coating in a 25-sccm argon ambient with a spray coating power rating of 80 W and a pressure of 30 mTorr. Next, an approximately 17-nanometer gadolinium oxide is deposited on the aluminum oxide film using e-beam evaporation. Besides, the iridium oxide film, which acts as the top electrode, is formed by RF spray coating as well in a 1:1 argon and oxygen ambient. By using the above procedure, a memory structure of iridium oxide/gadolinium oxide/aluminum oxide/titanium nitride is prepared. Please refer to FIG. 4. The multi-layer structure can be observed and the thickness of aluminum oxide and gadolinium oxide are 2 and 17 nanometers, respectively. In addition, FIG. 5 shows an energy-dispersive-spectroscopy (EDS) depth profile from the bottom electrode to the top electrode according to a preferred embodiment of the present invention.

Figure 6A:
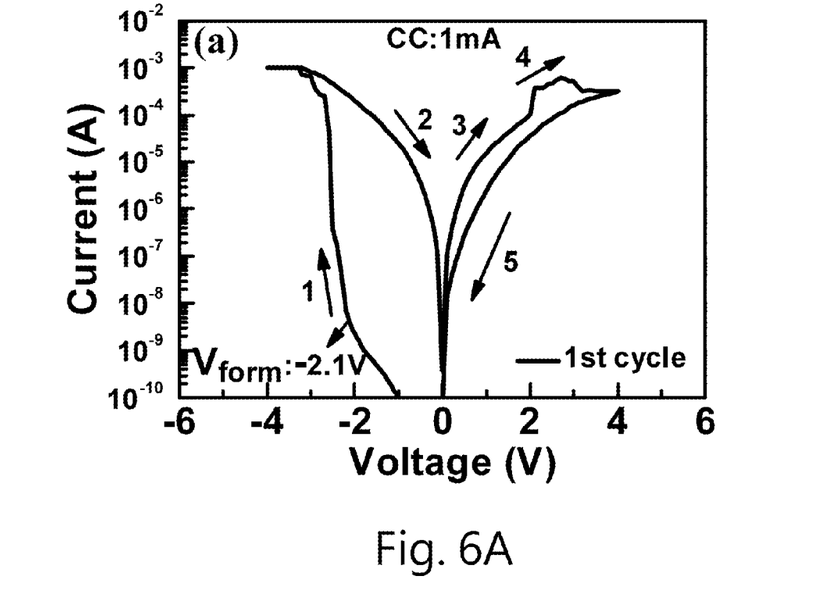
FIG. 6A and FIG. 6B shows a current-voltage test diagram according to a preferred embodiment of the present invention.
Figure 6B:
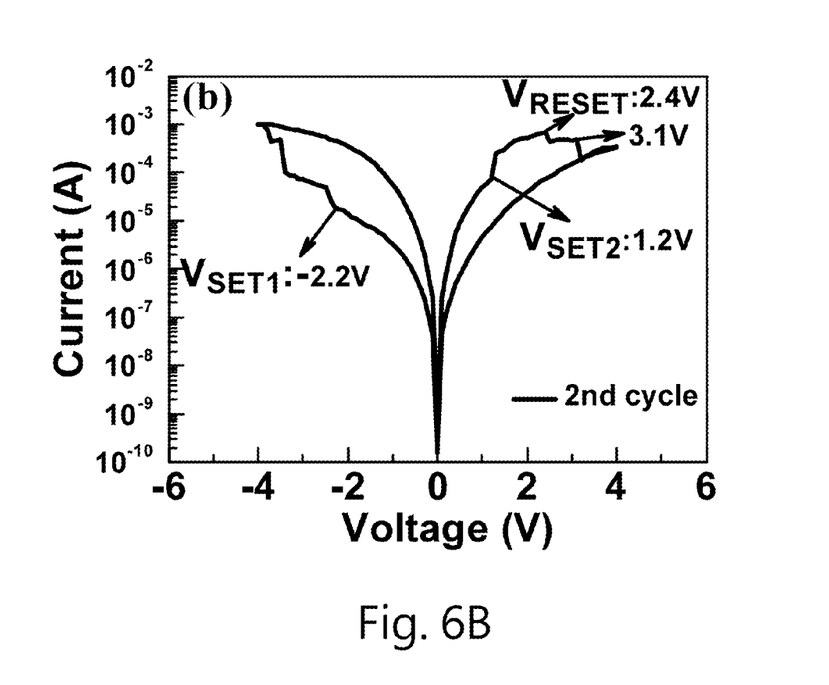

Please refer to FIG. 6A and FIG. 6B, which shows the bipolar I-V switching characteristics of the memory having the stack structure of iridium oxide/gadolinium oxide ($GdO_x$)/aluminum oxide/titanium nitride. The voltage sweeping direction follows the arrows from 1 to 5. The voltage sweeps in the order of $0V \to -4V \to 0V \to +4V \to 0V$. Besides, the current compliance (CC) is 1 mA.

Figure 7A:
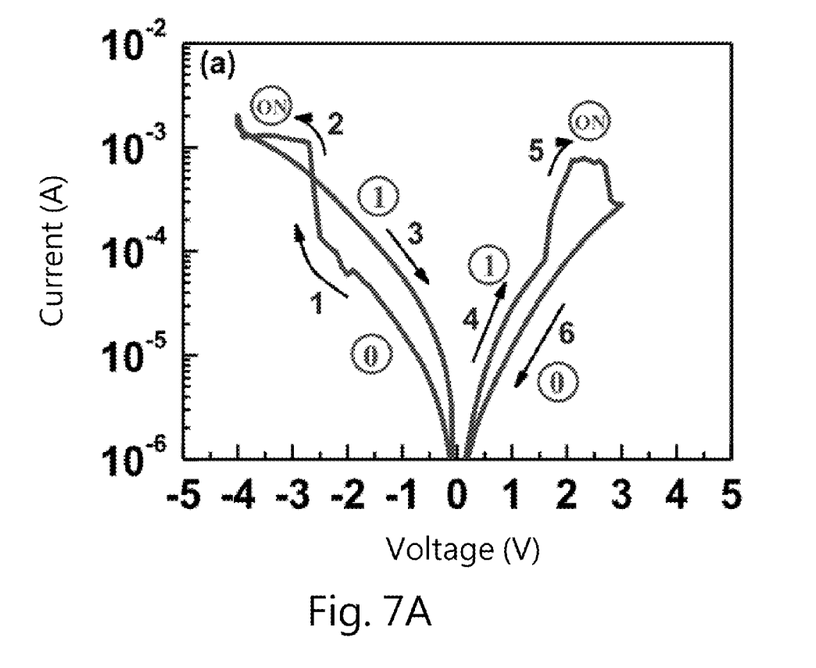
FIG. 7A shows a current-voltage test diagram according to a preferred embodiment of the present invention, used for highlighting the typical CRS feature.
Figure 7B:
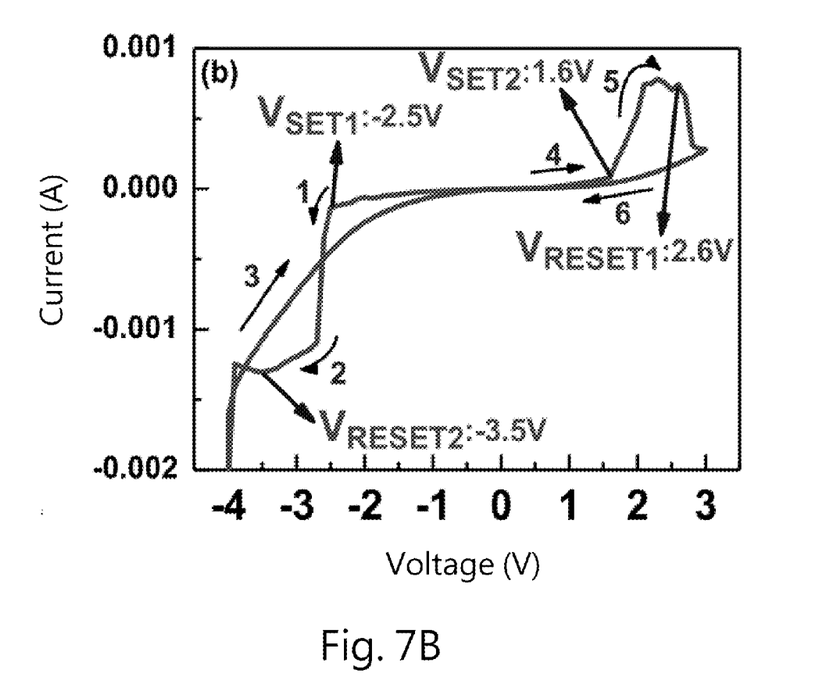
FIG. 7B shows a current-voltage test diagram according to a preferred embodiment of the present invention, used for illustrating the CRS feature in the linear scale.

Please refer to FIG. 7A, which shows the typical CRS feature of the memory according to the present invention after a +3V adjusting voltage is applied. In FIG. 7B, the CRS feature is illustrated in the linear scale. As shown in the figures, the switching direction follows the arrows 1 to 6; the CRS states are represented by 0, ON, and 1. According to the present embodiment, the memory switches to ON at the arrows $1 \to 2$ and $4 \to 5$, respectively, under the conditions of $V_{SET1}=-2.5V$ and $V_{SET2}=1.6V$. In addition, it switches to 1 or 0 at the arrows $2 \to 3$ and $5 \to 6$, respectively, under the conditions of $V_{RESET2}=-3.5V$ and $V_{RESET1}=2.6V$.

Figure 8:
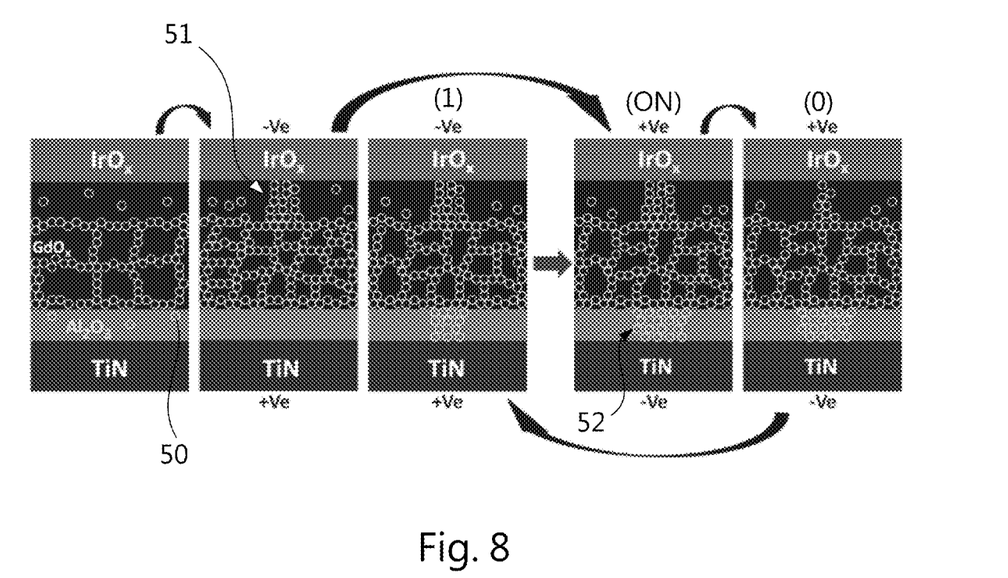
FIG. 8 shows the performance of filament paths formed by oxygen vacancies in different memory states according to a preferred embodiment of the present invention.

Please refer to FIG. 8. As described above, the present invention adopts specific materials and includes an additional dielectric film. By using the stack structure of top electrode/dielectric/dielectric/bottom electrode, instead of the normal BS feature, the feature of a CRS memory is achieved. The reason is that after the memory structure is formed, taking $GdO_x$ as the second dielectric film for example, the Gd—O bond will break at the grain boundary of the $GdO_x$ film. The formed oxygen vacancies carry positive charges. By applying a negative bias (−Ve), they will move towards the top electrode. In FIG. 8, the filament paths 51 formed by these oxygen vacancies 50 are close to the interface between the $GdO_x$ film and the top electrode. These conductive filament paths are greater than the filament paths of a normal BS memory. This is because the second dielectric film should be made thinner given the combination of the first and second dielectric films, and hence forming more oxygen vacancies. By testing, the LRS according to the present embodiment of the present invention is lower than that of a normal BS memory by 50%.

If a positive voltage is applied, in a general BS memory, the oxygen vacancies will move towards the $GdO_x$ film and break the filament paths. Thereby, SET will not appear after RESET, meaning that the memory window is collapsed. On the contrary, the memory fabricated according to the present embodiment of the present invention can have the $V_{SET2}$ equal to 1.6V. This is because the filament paths 52 composed by oxygen vacancies are formed in the $Al_2O_3$ film, which acts as the first dielectric film, and hence entering the ON state. As the voltage is further increased to 2.6V, the filament paths close to the top electrode and the $GdO_x$ film will be reduced or break, and thereby entering the 0 state. When $V_{RESET2}$ is applied, the filament paths will shrink or rupture, and thus entering the 1 state.

In addition to providing memory functions, the present invention can be further applied to biological tests and used as a biological test memory. In the structure of the present invention, the top surface of the top electrode can be used as the contact surface with the sample. The current changes caused by sample contact are then used as the basis for detection.

The material of the top electrode according to the present invention is iridium oxide, which can be involved in the oxidation and reduction reactions with $H_2O_2$ and consequently changing the pH value of the solution. Then the location can have detectable current or voltage variations. Take the sample mixed by serum and benzyl amine for example. The sample will first have the following reaction:

$LOXL2+C_6H_5CH_2NH_2 \to H_2O_2$ (Reaction 1)

The enzyme LOXL2 in the serum will react with the benzyl amine and produce hydrogen peroxide. It means that if hydrogen peroxide is found in the sample, then the serum contains the enzyme LOXL2. According to the present invention, the sample contacts the top electrode made of iridium oxide. When iridium contacts hydrogen peroxide, the following reactions will occur:

$H_2O_2+IrO_x \to Ir^{3+}+2H^++2O_2$ (Reaction 2)

$Ir^{3+}+H_2O_2+2H^+ \to Ir^{4+}+2H_2O$ (Reaction 3)

In the Reaction 2, hydrogen peroxide reduces inorganic oxide to inorganic ions $Ir^{3+}$; hydrogen peroxide acts as a reducing agent; and the product is oxygen. In the Reaction 3, hydrogen peroxide further oxidizes $Ir^{3+}$ to $Ir^{4+}$ in an acid ambient and the product is water. According to the present invention, after the sample contacts the iridium oxide film, the reactions are not limited to the Reaction 2 or 3 as described above. Instead, depending on the concentration of hydrogen peroxide, more oxidation or more reduction reactions can occur. Nonetheless, the present invention does not limit to requiring more $Ir^{3+}$ or $Ir^{4+}$. It suffices once iridium ions are produced. Iridium ions will be produced by the oxidation and/or reduction reactions between iridium oxide and hydrogen peroxide, and then detectable voltage changes will occur. Basically, the work function of iridium oxide will increase by increasing $H_2O_2$ concentration as well as current conduction changes. However, pH value of test sample remains unchanged during concentration change of $H_2O_2$. The memory according to the present invention is applied in test. When it is used as a bio-medical resistive random access memory (BM-RRAM), it can detect sensitively and real-timely if the enzyme LOXL2 is contained in serum and thus evaluating the risk of cancers.

Figure 9:
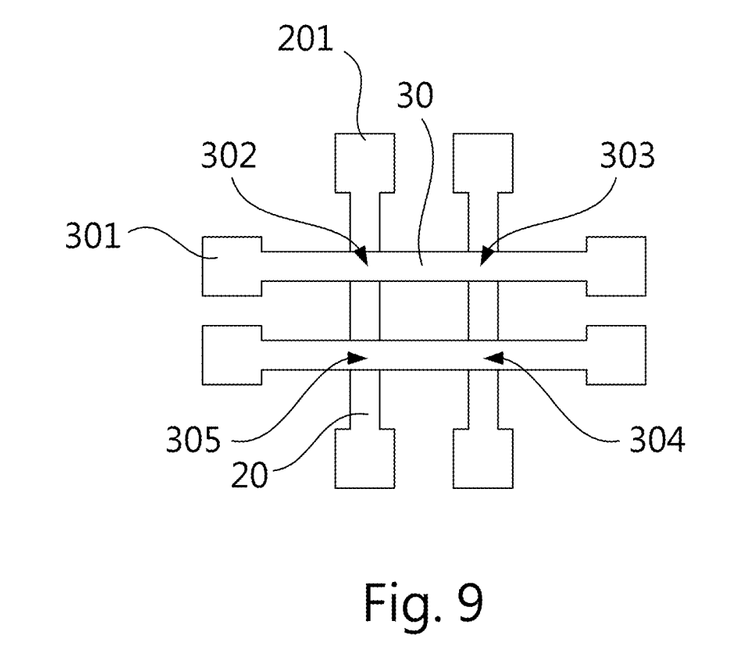
FIG. 9 shows a schematic diagram of a portion of the memory structure according to a preferred embodiment of the present invention, used for illustrating a test unit for biological test.
Figure 10:
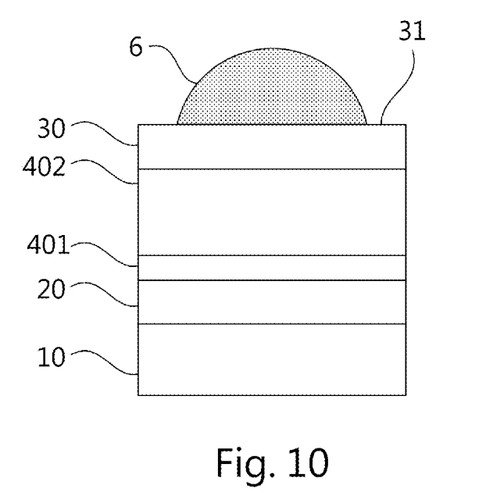
FIG. 10 shows a schematic diagram of the stack structure of the middle layer according to a preferred embodiment of the present invention, used for illustrating a sample contacting the top surface.
Figure 11:
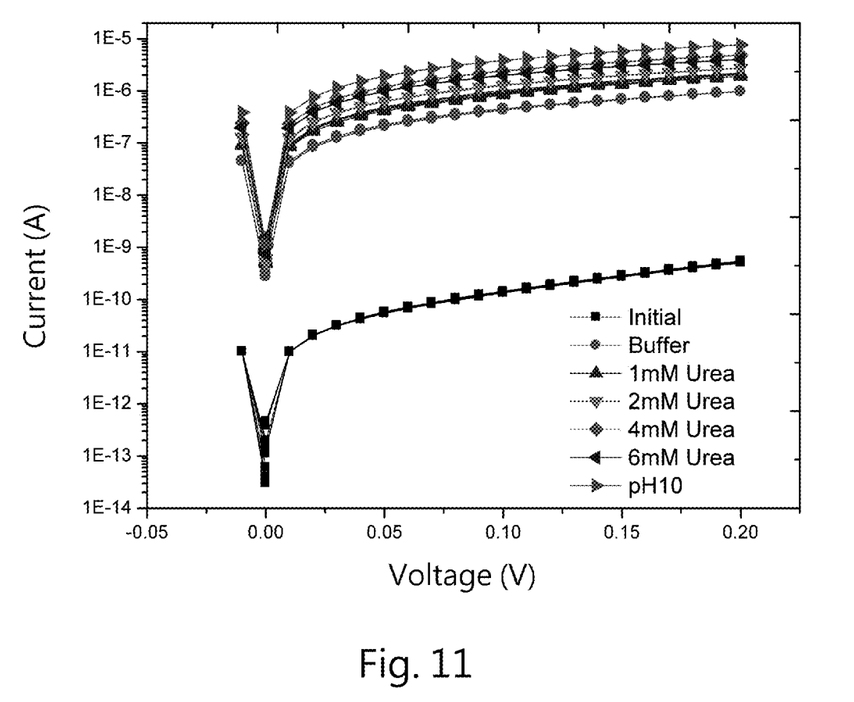
FIG. 11 shows current-voltage test results by using urea with different concentrations as the samples according to a preferred embodiment of the present invention.

Please refer to FIG. 9. When the present invention is used as a BM-RRAM, according to an embodiment, a 2*2 array having cross points 302, 303, 304, 305 is a test unit. The cross point 302 is a serum sample with a pH value adjusted to 7.4 and used for detecting the enzyme LOXL2 and evaluating the risk of breast cancer. The cross point 3.3 is a pH7.4 solution and used as a reference point. The cross point 304 is a urine sample with a pH value adjusted to 7.4 and used for detecting sarcosine and evaluating the risk of prostate cancer. The cross point 305 is a pH7.4 solution containing acetylcholine. The test method is to contact the liquid with the top electrodes at the cross points. Please refer to FIG. 10, the sample 6 contacts a top surface 31 of the bit line 30 acting as the top electrode. In FIG. 11, the current changes of urea sample of different concentrations by various biases are disclosed. The principle is that urea ($CO(NH_2)_2$) can dissociate into $NH_4^+$ and OFF under the assistance of urease. The changes in the conductivity prove the feasibility of using the present invention as a BM-RRAM. A single cross-point is used for this measurement.

In the structure used as a BM-RRAM according to an embodiment of the present invention, the material of the first dielectric film is aluminum oxide ($Al_2O_3$) or gadolinium oxide ($Gd_2O_3$); the material of the second dielectric film can be similar as that of the first dielectric film. The first dielectric material is stoichiometry, larger band gap, and less defective, where as the second dielectric is non-stoichiometry, lower band gap and huge defective (or oxygen vacancy). In addition, the first dielectric can be used on the second dielectric or second dielectric/to electrode interface or electrode/dielectric/dielectric/dielectric/electrode structure for cross-point arrays. Alternatively, the material of the second dielectric film can be gadolinium oxide or aluminum oxide and different from that of the first dielectric film. Therefore, the oxygen vacancy can be formed or ruptured at the bottom electrode/dielectric interface or dielectric/top electrode interface under alternative plurality. The silicon dioxide ($SiO_2$) can be used as a first dielectric also. The material of the bottom electrode can be selected form titanium nitride or tungsten or other inert electrode. Besides, in terms of thickness control, the total thickness of the first and second dielectric films is approximately 10 to 40 nanometers. The thickness of the iridium oxide film, which acts as the top electrode, is approximately 2 to 20 nanometers. Its top surface can further include multiple nanometer micro holes for improving the reaction efficiency. One of the advantages of using the present invention as a BM-RRAM is to improve the test speed to within several nanoseconds. In addition, current changes as small as about few nanoamperes can be detected, which means that the concentration of the test target, such as the enzyme LOXL2, or sarcosine, can be smaller than pM. Thereby, the present invention owns the properties of high sensitivity and high reactivity.

Furthermore, when the present invention is applied to BM-RRAM, the operational steps can be summarized as:

Step S1: Using a top electrode to apply voltage/current and bottom electrode grounded, and acquiring a first voltage/current or resistance at a single cross point;

Step S2: Dispose a sample on that cross-point and acquiring a second voltage/current or resistance; and Step S3: Comparing the first voltage/current (or resistance) and the second voltage/current (or resistance) for acquiring a difference; using the difference to judge the content of the test target in the sample; and the test target is the enzyme LOXL2 or sarcosine as described above. Due to the nonvolatile memory, data will store without erase.

Step S4: After RESET to the same resistance state or '0' state of four cross points, one cross point will measure a small amount of blood drop (or urine); second cross point will measure benzyl-amine plus a small amount of blood drop (or urine); third cross point will measure enzyme of sarcosine plus a small amount of blood drop (or urine); and forth cross point will measure urease plus a small amount of blood drop (or urine). The data will compare between these cross points. Similarly, many cross points will be used to measure multi-analytes at the same time. Data will store in this cross point arrays unless RESET next. After clean these cross points it will be used again or many times for testing.

To sum up, the present invention discloses in detail a memory structure. The structure includes an interface between iridium oxide and a specific dielectric and thus preferably facilitating formation oxygen vacancy filament paths and exhibiting the CRS memory feature. The present invention can also be used as a BM-RRAM. It uses a plurality of cross points of the word lines and bit lines in the memory as a part of the biochip. By disposing the sample on the bit line, which acts as the top electrode, the iridium oxide in the material of the bit line will have oxidation and reduction reactions and produce detectable current or voltage changes and hence giving the concentration of test target, for example, the enzyme LOXL2 or sarcosine, in the sample. Thereby, the possibility of suffering from breast or prostate cancer can be evaluated. Given the multiple functions and excellent properties, the present invention is undoubtedly a valuable memory structure worthy of developing the health care unit at home.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. A memory structure, comprising:
   a substrate;
   a plurality of word lines, disposed in parallel on said substrate;
   a plurality of bit lines, disposed in parallel on said substrate, perpendicular to the parallel direction of said plurality of word lines, interlacing with and covering said plurality of word lines at a plurality of cross points, and the material of said plurality of bit lines being iridium oxide, ruthenium oxide, platinum, palladium, cobalt, rhenium, rhodium, or graphene; and
   a plurality of middle layers disposed at said plurality of cross points and located between said plurality of word lines and said plurality of bit lines and including a first dielectric film and a second dielectric film arranged bottom-up sequentially;
   where the material of said second dielectric film is selected from the group consisting of gadolinium oxide, hafnium oxide, tantalum oxide, nickel oxide, zirconium oxide, chromium oxide, titanium oxide, tungsten oxide, cerium oxide, and germanium oxide; wherein a top surface of said plurality of bit lines includes a plurality of nanometer micro holes.

2. The memory structure of claim 1, wherein the material of said plurality of word lines is titanium nitride.

3. The memory structure of claim 1, wherein one or more end of said plurality of word lines includes a bottom electrode.

4. The memory structure of claim 1, wherein one or more end of said plurality of bit lines includes a top electrode.

5. The memory structure of claim 1, wherein said substrate includes a silicon layer and a silicon oxide layer.

6. The memory structure of claim 1, wherein the material of said first dielectric film is aluminum oxide or silicon dioxide.

7. A memory structure, comprising:
   a substrate;
   a plurality of word lines, disposed in parallel on said substrate;
   a plurality of bit lines, disposed in parallel on said substrate, perpendicular to the parallel direction of said plurality of word lines, interlacing with and covering said plurality of word lines at a plurality of cross points, and the material of said plurality of bit lines being iridium oxide, ruthenium oxide, platinum, palladium, cobalt, rhenium, rhodium, or graphene; and
   a plurality of middle layers disposed at said plurality of cross points and located between said plurality of word lines and said plurality of bit lines and including a first dielectric film and a second dielectric film arranged bottom-up sequentially;

where the material of said second dielectric film is gadolinium oxide, hafnium oxide, tantalum oxide, nickel oxide, zirconium oxide, chromium oxide, titanium oxide, tungsten oxide, cerium oxide, or germanium oxide; a top surface of said plurality of bit lines is used for contacting a sample; and said sampled includes urine, serum or blood; wherein said top surface includes a plurality of nanometer micro holes.

8. The memory structure of claim 7, wherein the material of said first dielectric film is the same as the material of said second dielectric film.

9. The memory structure of claim 7, wherein one of said plurality of cross points is used as the reference point.

* * * * *